United States Patent
Kimura et al.

(10) Patent No.: US 11,253,281 B2
(45) Date of Patent: Feb. 22, 2022

(54) MEDICAL TREATMENT TOOL

(71) Applicant: OLYMPUS CORPORATION, Tokyo (JP)

(72) Inventors: Kayuri Kimura, Saitama (JP); Masatoshi Iida, Tokyo (JP); Noriaki Yamanaka, Tokyo (JP); Shuya Jogasaki, Tokyo (JP); Yoshiyuki Kumada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 310 days.

(21) Appl. No.: 16/376,685

(22) Filed: Apr. 5, 2019

(65) Prior Publication Data

US 2019/0231374 A1    Aug. 1, 2019

Related U.S. Application Data

(63) Continuation of application No. PCT/JP2016/085237, filed on Nov. 28, 2016.

(51) Int. Cl.
*A61B 17/29* (2006.01)
*A61B 17/00* (2006.01)
*A61B 34/00* (2016.01)

(52) U.S. Cl.
CPC ........ *A61B 17/29* (2013.01); *A61B 17/00234* (2013.01); *A61B 34/71* (2016.02);
(Continued)

(58) Field of Classification Search
CPC .... A61B 2017/2929; A61B 2017/2932; A61B 2017/2933; A61B 2017/2938;
(Continued)

(56) References Cited

U.S. PATENT DOCUMENTS 5,507,773 A   4/1996  Huitema et al.
5,562,700 A   10/1996 Huitema et al.
(Continued)

FOREIGN PATENT DOCUMENTS

EP   0668057 A2   8/1995
EP   0800792 A1   10/1997
(Continued)

OTHER PUBLICATIONS

Japanese Office Action dated Jul. 21, 2020 in Japanese Patent Application No. 2017-521884.
(Continued)

*Primary Examiner* — Majid Jamialahmadi
(74) *Attorney, Agent, or Firm* — Scully, Scott, Murphy & Presser, P.C.

(57) ABSTRACT

A medical treatment tool includes an elongated insertion section; a grasper supported by a distal end of the insertion section so as to be openable and closable; a generator disposed at a proximal end of the insertion section and generating a force to drive the grasper; a transmitter transmitting the force generated by the generator to the distal end of the insertion section; an amplifier amplifying the force transmitted through the transmitter; and a toggle amplifying and converting the force amplified by the amplifier into a force directed to open or close the grasper.

4 Claims, 7 Drawing Sheets

(52) U.S. Cl.
CPC ............ *A61B 2017/00323* (2013.01); *A61B 2017/2902* (2013.01); *A61B 2017/2905* (2013.01); *A61B 2017/2923* (2013.01); *A61B 2017/2936* (2013.01); *A61B 2017/2939* (2013.01); *A61B 2017/2943* (2013.01)

(58) Field of Classification Search
CPC .... A61B 2017/2939; A61B 2017/2941; A61B 2017/2936; A61B 2017/2919; A61B 2017/2922; A61B 34/30; A61B 34/71; A61B 34/70
See application file for complete search history.

(56) References Cited

U.S. PATENT DOCUMENTS

| | | | |
|---|---|---|---|
| 5,562,701 | A | 10/1996 | Huitema et al. |
| 5,562,702 | A | 10/1996 | Huitema et al. |
| 6,206,903 | B1 | 3/2001 | Ramans |
| 6,896,704 | B1 | 5/2005 | Higuchi et al. |
| 7,316,681 | B2 | 1/2008 | Madhani et al. |
| 8,333,780 | B1 | 12/2012 | Pedros et al. |
| 10,016,207 | B2 | 7/2018 | Suzuki et al. |
| 10,343,291 | B2 | 7/2019 | Jogaski et al. |
| 2002/0040217 | A1 | 4/2002 | Jinno |
| 2004/0267406 | A1 | 12/2004 | Jinno |
| 2006/0167589 | A1 | 7/2006 | Jinno |
| 2007/0288044 | A1 | 12/2007 | Jinno et al. |
| 2008/0039255 | A1 | 2/2008 | Jinno et al. |
| 2008/0232932 | A1 | 9/2008 | Jinno |
| 2009/0110533 | A1 | 4/2009 | Jinno |
| 2009/0112229 | A1 | 4/2009 | Omori et al. |
| 2009/0112230 | A1 | 4/2009 | Jinno |
| 2010/0198253 | A1 | 8/2010 | Jinno et al. |
| 2012/0239011 | A1 | 9/2012 | Hyodo et al. |
| 2014/0249545 | A1* | 9/2014 | Hyodo .................. A61B 34/30 606/130 |
| 2015/0025571 | A1 | 1/2015 | Suzuki et al. |
| 2017/0135710 | A1 | 5/2017 | Hasegawa et al. |
| 2018/0050456 | A1 | 2/2018 | Yamanaka |
| 2019/0059922 | A1 | 2/2019 | Yamanaka |

FOREIGN PATENT DOCUMENTS

| | | |
|---|---|---|
| EP | 1 195 151 A1 | 4/2002 |
| EP | 1854418 A1 | 11/2007 |
| EP | 1886630 A2 | 2/2008 |
| EP | 2077095 A2 | 7/2009 |
| EP | 2666429 A1 | 11/2013 |
| EP | 2837341 A1 | 2/2015 |
| EP | 3263053 A1 | 1/2018 |
| FR | 1500906 A | 11/1967 |
| JP | H01-199777 A | 8/1989 |
| JP | 2000-325375 A | 11/2000 |
| JP | 2002-102248 A | 4/2002 |
| JP | 2002-103255 A | 4/2002 |
| JP | 2007-301692 A | 11/2007 |
| JP | 2008-036793 A | 2/2008 |
| JP | 2009-106606 A | 5/2009 |
| JP | 2009-107087 A | 5/2009 |
| JP | 2009-107095 A | 5/2009 |
| JP | 2010-221329 A | 10/2010 |
| JP | 2010-227331 A | 10/2010 |
| JP | 2010-253162 A | 11/2010 |
| JP | 2012-187311 A | 10/2012 |
| JP | 2013-215502 A | 10/2013 |
| WO | WO 2009/057347 A1 | 5/2009 |
| WO | WO 2010/090292 A2 | 8/2010 |
| WO | WO 2010/126129 A1 | 11/2010 |
| WO | WO 2013/154157 A1 | 10/2013 |
| WO | WO 2016/136676 A1 | 9/2016 |
| WO | 2016/194777 A1 | 12/2016 |
| WO | WO 2016/194067 A1 | 12/2016 |
| WO | 2017/195246 A1 | 11/2017 |

OTHER PUBLICATIONS

International Search Report and the Written Opinion dated Aug. 9, 2016 received in related International Application No. PCT/JP2016/065962.
Office Action dated Apr. 14, 2020 received in U.S. Appl. No. 15/801,356.
International Search Report dated Jan. 31, 2017 issued in PCT/JP2016/085237.
International Search Report dated Aug. 18, 2015 issued in PCT/JP2015/065633.
International Search Report dated Aug. 2, 2016 issued in PCT/JP2016/063728.
International Search Report dated Aug. 9, 2016 issued in PCT/JP2016/065611.
German Office Action dated Mar. 13, 2019 issued in DE 112016001915.7.

* cited by examiner

MEDICAL TREATMENT TOOL

CROSS-REFERENCE TO RELATED APPLICATIONS

This is a continuation of International Application PCT/JP2016/085237 which is hereby incorporated by reference herein in its entirety.

TECHNICAL FIELD

The present invention relates to a medical treatment tool.

BACKGROUND ART

A medical treatment tool that grasps body tissue and the like to perform a procedure is known (for example, refer to PTL 1). This medical treatment tool has a grasping unit at a distal end of an elongated insertion section, and the grasping unit is closed by a pulling force applied to an operation unit disposed at a proximal end of the insertion section. The pulling force is amplified by a toggle mechanism so that the grasping unit exerts a large grasping force.

CITATION LIST

Patent Literature

{PTL 1}
Japanese Unexamined Patent Application, Publication No. 2012-187311

SUMMARY OF INVENTION

According to an aspect of the present invention, there is provided a medical treatment tool including: an elongated insertion section; a grasper supported by a distal end of the insertion section so as to be openable and closable, the grasper including a pair of grasping pieces, at least one of which is rotatably supported relative to the insertion section; a generator disposed at a proximal end of the insertion section and generating a force to drive the grasper; a transmitter transmitting the force generated by the generator to the distal end of the insertion section; an amplifier amplifying the force transmitted through the transmitter; and a toggle amplifying and converting the force amplified by the amplifier into a force directed to open or close the grasper. The toggle includes a pair of links each having a first end and a second end, the first ends being rotatably connected to proximal end portions of the respective grasping pieces, the second ends being rotatably connected to each other and being supported so as to be movable along a movement axis extending in a longitudinal direction of the insertion section; the pair of links have a length larger than a distance between the second end and the movement axis; and a length of a line segment connecting the second end to a rotation center of the grasping pieces and being projected onto the movement axis is smaller than a length of a line segment connecting the first end and the rotation center and being projected onto the movement axis. The transmitter is a wire that transmits a pulling force along the longitudinal direction of the insertion section. The amplifier includes a movable pulley supported by the wire wrapping around the movable pulley so as to be movable in the longitudinal direction of the insertion section, the movable pulley having a rotation shaft connected to the second ends. The wire has a proximal end connected to the generator, has two segments that extend substantially parallel to each other on respective sides of the movable pulley so as to flank the rotation shaft of the movable pulley, and has another end fixed to the insertion section.

According to another aspect of the present invention, there is provided a medical treatment tool including: an elongated insertion section; a grasper supported by a distal end of the insertion section so as to be openable and closable, the grasper including a pair of grasping pieces, at least one of which is rotatably supported relative to the insertion section; a generator disposed at a proximal end of the insertion section and generating a force to drive the grasper; a transmitter transmitting the force generated by the generator to the distal end of the insertion section; an amplifier amplifying the force transmitted through the transmitter; and a toggle amplifying and converting the force amplified by the amplifier into a force directed to open or close the grasper. The toggle includes a pair of links each having a first end and a second end, the first ends being rotatably connected to proximal end portions of the respective grasping pieces, the second ends being rotatably connected to each other and being supported so as to be movable along a movement axis extending in a longitudinal direction of the insertion section; the pair of links have a length larger than a distance between the second end and the movement axis; and a length of a line segment connecting the second end to a rotation center of the grasping pieces and being projected onto the movement axis is smaller than a length of a line segment connecting the first end and the rotation center and being projected onto the movement axis. The transmitter is a wire that transmits a pulling force along the longitudinal direction of the insertion section. The amplifier includes a fixed pulley around which the wire is wrapped, the fixed pulley being supported so as to be rotatable about a shaft fixed to the insertion portion.

According to another aspect of the present invention, there is provided a medical treatment tool including: an elongated insertion section; a grasper supported by a distal end of the insertion section so as to be openable and closable; a generator disposed at a proximal end of the insertion section and generating a force to drive the grasper; a transmitter transmitting the force generated by the generator to the distal end of the insertion section; an amplifier amplifying the force transmitted through the transmitter; and a toggle amplifying and converting the force amplified by the amplifier into a force directed to open or close the grasper. The amplifier is a second toggle disposed between the transmitter and the toggle.

DESCRIPTION OF EMBODIMENTS

A medical treatment tool 1 according to one embodiment of the present invention will now be described with reference to the drawings.

Figure 1:
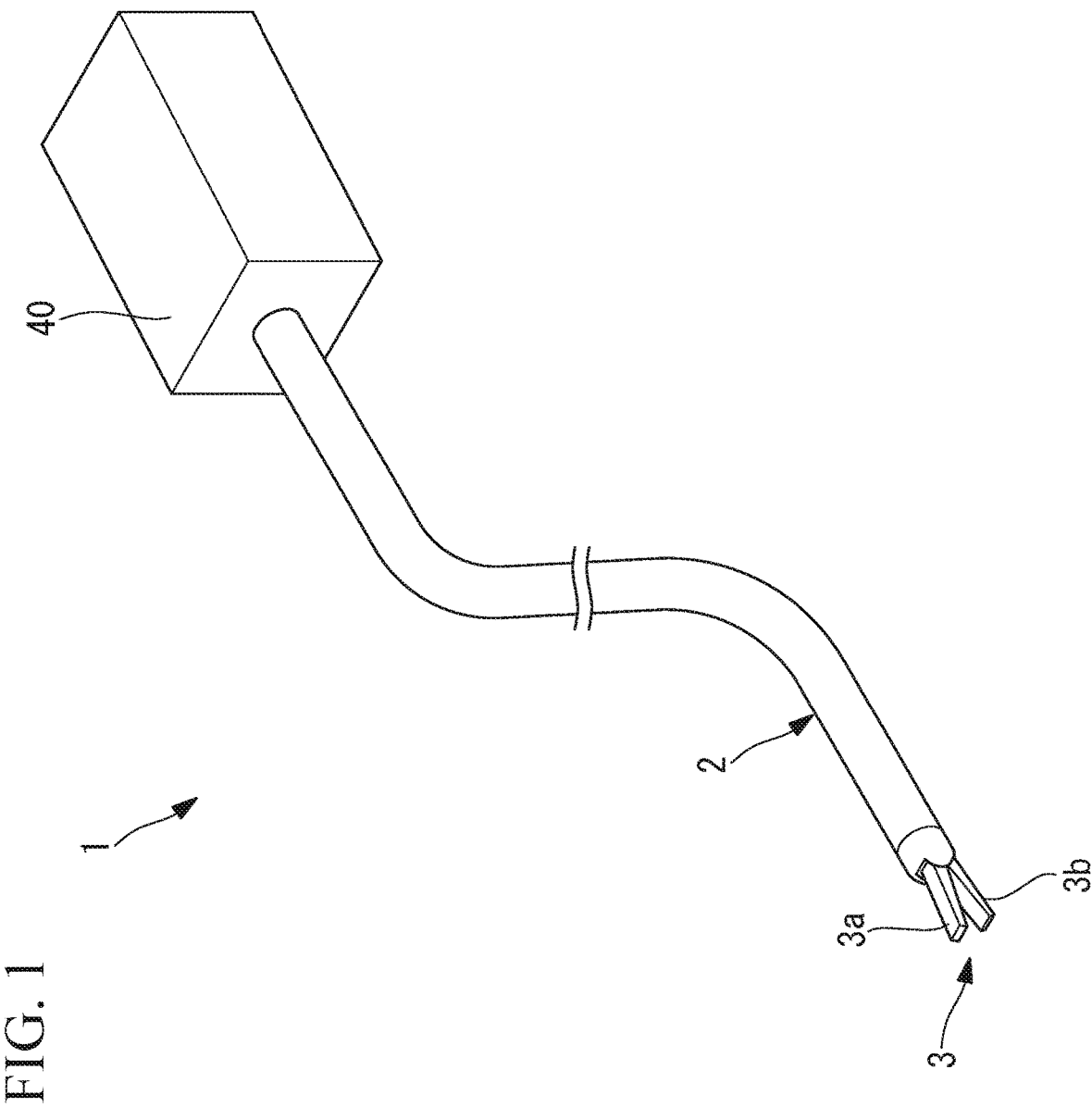
FIG. 1 is a perspective view of a medical treatment tool according to one embodiment of the present invention.
Figure 2:
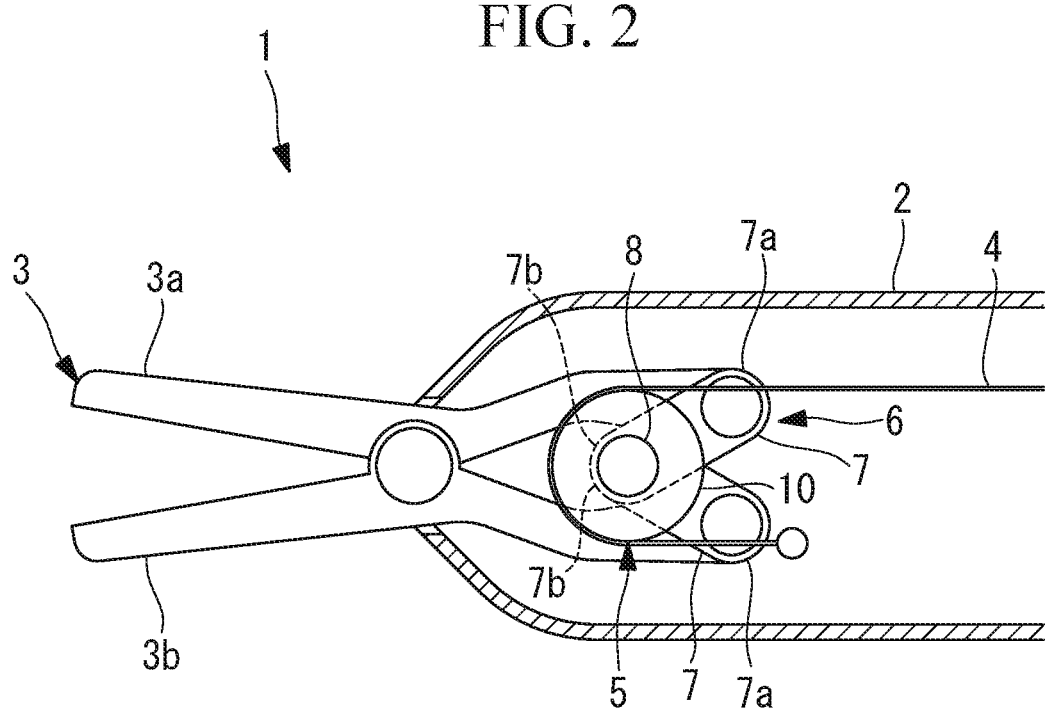
FIG. 2 is a longitudinal sectional view of a distal end portion of the medical treatment tool according to the embodiment of the present invention, in which distal ends of grasping pieces are in an open state.

As illustrated in FIGS. 1 and 2, the medical treatment tool 1 according to this embodiment includes an elongated flexible insertion section 2, a grasping unit 3 disposed at a distal end of the insertion section 2, a driving unit 40 disposed at a proximal end of the insertion section 2, a wire (force transmitting member) 4 that transmits the pulling force generated by the driving unit 40, an amplifying mechanism (force amplifying mechanism) 5 that amplifies the pulling force, and a toggle mechanism 6 that converts the force amplified by the amplifying mechanism 5 into a force that opens and closes the grasping unit 3.

The grasping unit 3 includes a pair of grasping pieces 3a and 3b that are supported by a rotation center, which is fixed to the insertion section 2 and extends in a direction orthogonal to the longitudinal axis of the insertion section 2, so as to be pivotable about the rotation center. A force acting in a direction that widens the gap between proximal-side end portions of the grasping pieces 3a and 3b with respect to the rotation center causes the grasping pieces 3a and 3b to move in a direction such that the distal ends thereof close and grasp the subject to be treated.

The driving unit 40 is where a pulling force is generated either electrically or manually, and is configured to apply the generated pulling force to the proximal end of the wire 4.

The toggle mechanism 6 is constituted by pivotably connecting ends (first ends) 7a of two link members 7, which have other ends (second ends) 7b pivotably connected to each other, to respective proximal-side end portions of the grasping pieces 3a and 3b.

Figure 3:
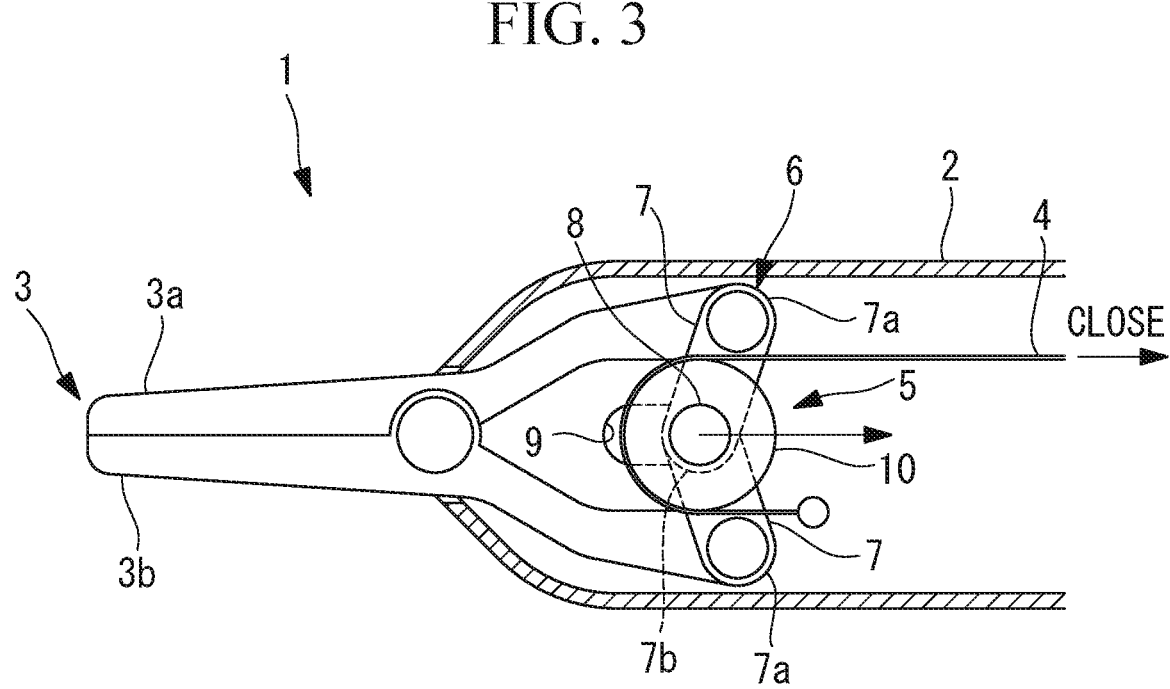
FIG. 3 is a longitudinal sectional view of the distal end portion of the medical treatment tool illustrated in FIG. 2, in which the distal ends of the grasping pieces are in a closed state.

As illustrated in FIG. 3, a connecting shaft (rotation shaft) 8 that pivotably connects the second ends 7b of the two link members 7 is contained in a slit 9, which is formed in the insertion section 2 and extends along the longitudinal direction, and supported by the slit 9 so as to be movable in the longitudinal direction.

As illustrated in FIG. 2, in a state in which the distal ends of the pair of grasping pieces 3a and 3b are open, the connecting shaft 8, which has moved along the slit 9, takes a position on the distal end side in the longitudinal direction. As illustrated in FIG. 3, in a state in which the distal ends of the pair of grasping pieces 3a and 3b are closed, the connecting shaft 8 takes a position on the proximal end side in the longitudinal direction.

As illustrated in FIG. 3, the connecting shaft 8 takes the proximal-most position as the distal ends of the pair of grasping pieces 3a and 3b are closed. Even in such a state, the connecting shaft 8 is located slightly on the distal end side with respect to a straight line connecting the first ends 7a of the two link members 7.

The distance between the movement axis extending in the longitudinal direction along the center of the slit 9 and the first end 7a of each link member 7 is set to be always shorter than the length of the link member 7.

Furthermore, the length of a line segment that connects the rotation center of the pair of grasping pieces 3a and 3b and the connecting shaft 8 and is projected onto the movement axis is set to be always smaller than the length of a line segment that connects the rotation center and the first end 7a and is projected onto the movement axis.

The amplifying mechanism 5 is equipped with a movable pulley 10 rotatably supported by the connecting shaft 8. A wire 4 extending from the proximal end side of the insertion section 2 in the longitudinal direction is wrapped around the movable pulley 10 and folded back, and the distal end of the wire 4 is fixed to the insertion section 2. In this manner, the wire 4 has two segments that flank the connecting shaft 8 and extend from the movable pulley 10 toward the proximal end side.

The operation of the medical treatment tool 1 of this embodiment configured as described above will now be described.

In order to treat a treatment subject site with the medical treatment tool 1 of this embodiment, the insertion section 2 is inserted into the body from the distal end side, and the grasping unit 3 having the distal ends open is brought near the treatment subject site.

Then the driving unit 40 is actuated to generate a pulling force that pulls the wire 4 toward the proximal end side. The pulling force applied to the wire 4 is transmitted to the distal end of the insertion section 2 through the wire 4 and pulls the movable pulley 10, around which the wire 4 is wrapped, toward the proximal end side. Since the wire 4 wrapped around the movable pulley 10 has two segments flanking the connecting shaft 8 of the movable pulley 10 and extending substantially parallel to each other toward the proximal end side, pulling forces generated in the two segments of the wire 4 act on the connecting shaft 8 to which the movable pulley 10 is fixed, and thus the connecting shaft 8 is pulled toward the proximal end side with a force twice the pulling force.

In other words, the movable pulley 10 functions as a movable block and is caused to move by a distance reduced to one-half relative to the distance the wire 4 is moved by pulling. As a result, the force amplified to twice the pulling force of the wire 4 acts on the movable pulley 10 and is input to the connecting shaft 8, which is the input portion of the toggle mechanism 6. Thus, the connecting shaft 8 of the link members 7 constituting the toggle mechanism 6 is caused to move up to the position illustrated in FIG. 3, the gap between the first ends 7a connected to the proximal-side ends of the pair of grasping pieces 3a and 3b is widened with a large force amplified by the toggle mechanism 6, and a large edge force can thereby be generated at the distal ends of the grasping pieces 3a and 3b.

As described above, according to the medical treatment tool 1 of this embodiment, since the pulling force applied to the wire 4 is amplified by the amplifying mechanism 5 and then input to the toggle mechanism 6, the amplification in the toggle mechanism 6 can be kept small. In other words, the length of the link members 7 that determines the amplification ratio of the toggle mechanism 6 can be shortened, and the diameter of the insertion section 2 can be decreased.

In particular, by using a movable pulley 10 that functions as a movable block, the pulling force applied to the wire 4 extending in the longitudinal direction of the insertion section 2 can be amplified, and a large force acting in the longitudinal direction can be generated in the connecting shaft 8 by using a simple structure.

Moreover, there is an advantage in that, since the movable pulley 10 is rotatable about the connecting shaft 8 of the link members 7, the lengths of the toggle mechanism 6 and the amplifying mechanism 5 in the longitudinal direction can be decreased, and when a bending portion is formed in the insertion section 2, the length of a hard tip on the distal end side of the bending portion can be decreased.

Figure 4:
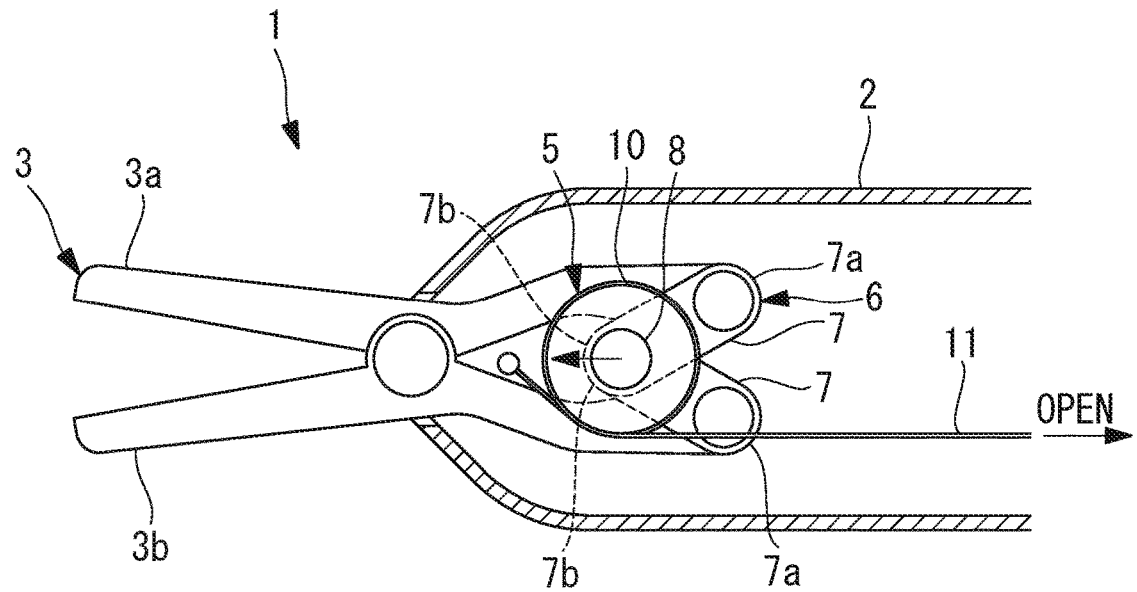
FIG. 4 is a longitudinal sectional view of a part of the distal end portion, illustrating the mechanism that opens the distal ends of the grasping pieces of the medical treatment tool illustrated in FIG. 2.

In this embodiment, the mechanism that opens the distal ends of the pair of grasping pieces 3a and 3b is not particularly limited. For example, a spring (not illustrated) may be installed so that the distal ends are constantly urged to open, or, as illustrated in FIG. 4, another wire 11 that moves the movable pulley 10 toward the distal end side when pulled toward the proximal end side may be wrapped around the movable pulley 10.

Figure 5:
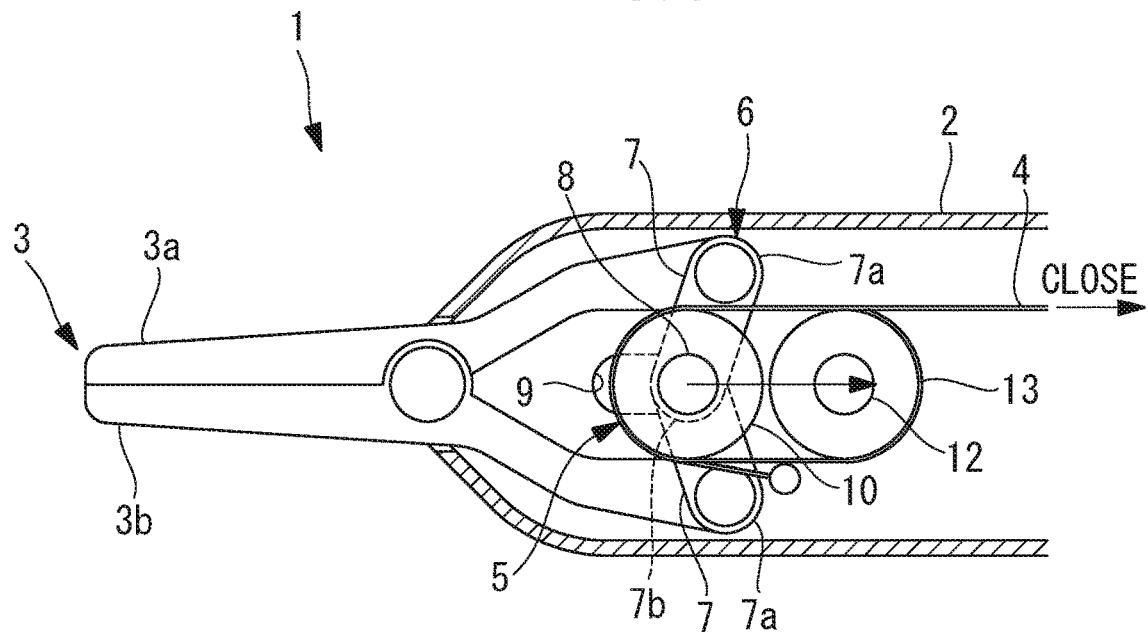
FIG. 5 is a longitudinal sectional view of a distal end portion illustrating a first modification of the medical treatment tool illustrated in FIG. 2.

In this embodiment, as illustrated in FIG. 5, a fixed pulley 13 supported by a shaft 12, which is fixed to the insertion section 2, so as to be rotatable about the shaft 12 may be installed, and the wire 4 wrapped around the movable pulley 10 may make two or more turns between the movable pulley 10 and the fixed pulley 13. Alternatively, there may be more than one set of a movable pulley 10 and a fixed pulley 13. In this manner, the pulling force can be amplified at an amplification ratio corresponding to the number of turns and input to the toggle mechanism 6.

Figure 6:
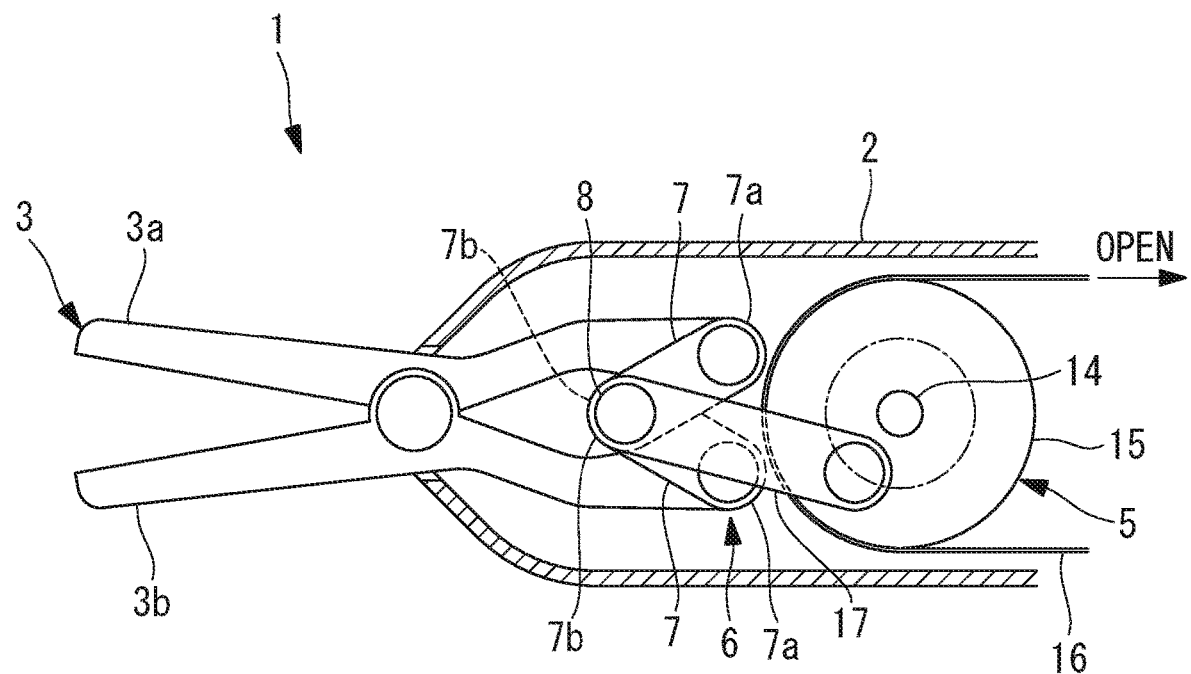
FIG. 6 is a longitudinal sectional view of a distal end portion according to a second modification of the medical treatment tool illustrated in FIG. 2, illustrating the operation of opening the distal ends of the grasping pieces.
Figure 7:
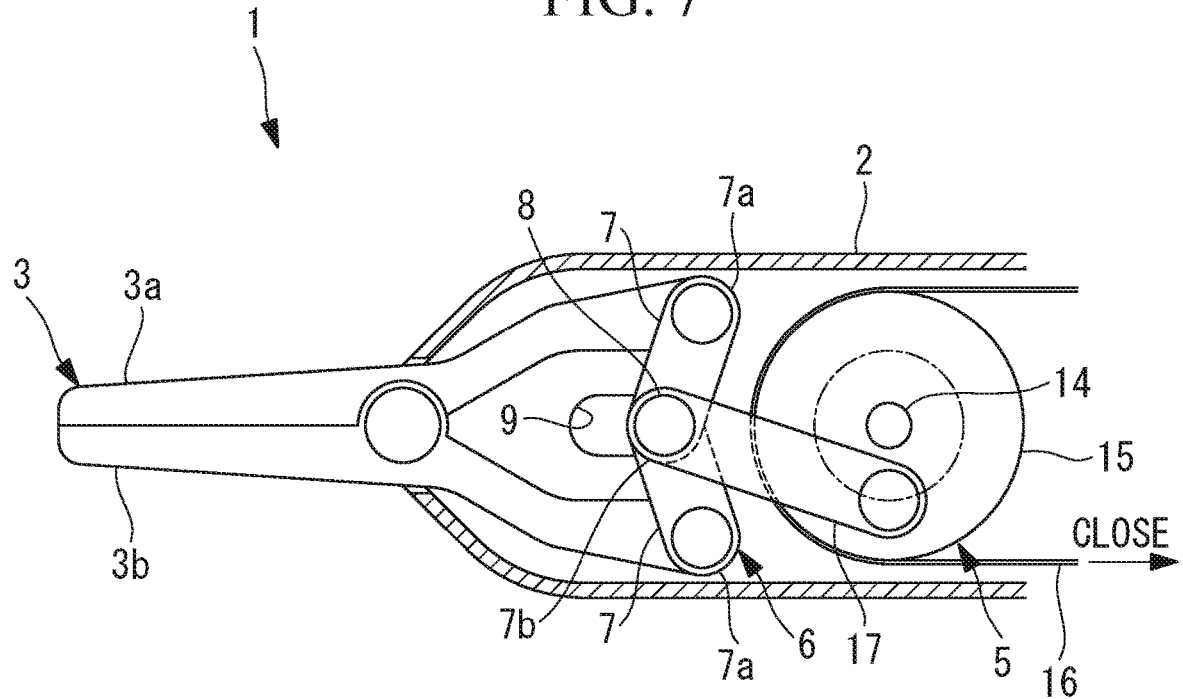
FIG. 7 is a longitudinal sectional view of the distal end portion of the medical treatment tool illustrated in FIG. 6, illustrating the operation of closing the distal ends of the grasping pieces.

As illustrated in FIGS. 6 and 7, instead of the movable pulley 10, the amplifying mechanism 5 may be a fixed pulley 15 supported by a shaft 14, which is fixed to the insertion section 2, so as to be rotatable about the shaft 14, and one end of a connecting link 17 may be pivotably connected to the connecting shaft 8 of the link members 7 of the toggle mechanism 6 while another end of the connecting link 17 may be pivotably connected to the fixed pulley 15 at a radially inner position from the outer circumferential surface around which a wire 16 is wrapped.

In this manner, a moment is generated in the fixed pulley 15 by the pulling force of the wire 16. Thus, a force larger than the pulling force can be generated in the connecting link 17 having a shorter moment arm, and the pulling force can be amplified and input to the toggle mechanism 6. In this case, as illustrated in FIGS. 6 and 7, the grasping unit 3 can be switched between open and close by switching the segment of the wire 16 to be pulled.

Figure 8:
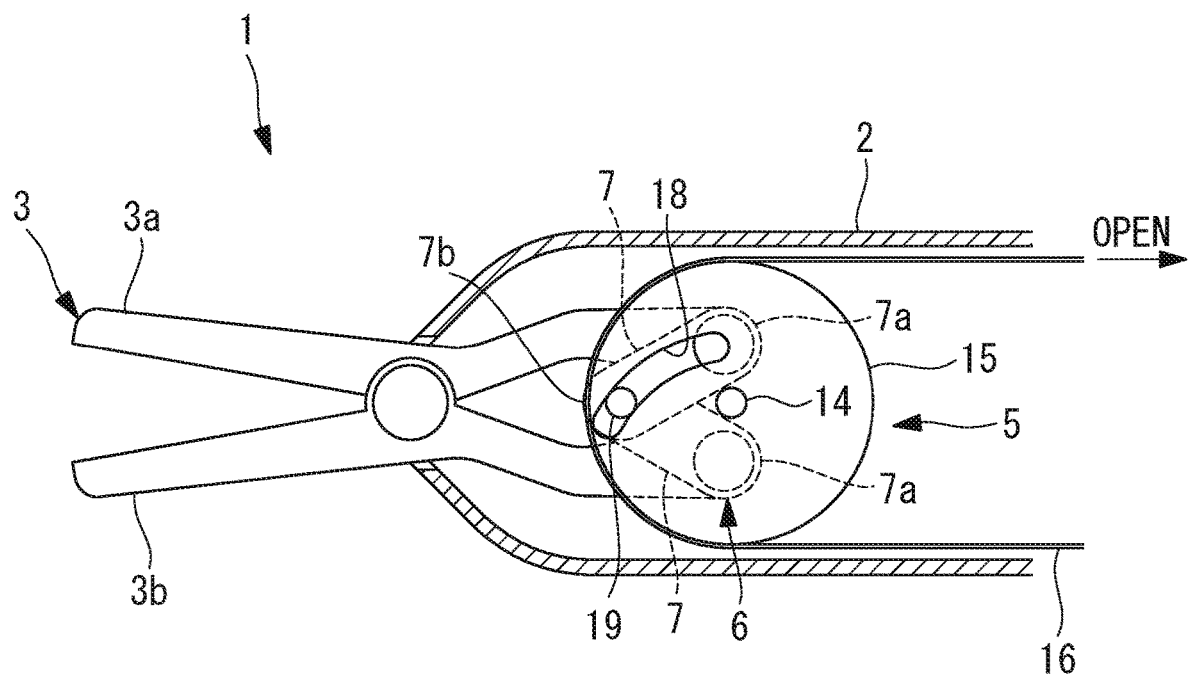
FIG. 8 is a longitudinal sectional view of a distal end portion according to a third modification of the medical treatment tool illustrated in FIG. 2, illustrating the operation of opening the distal ends of the grasping pieces.
Figure 9:
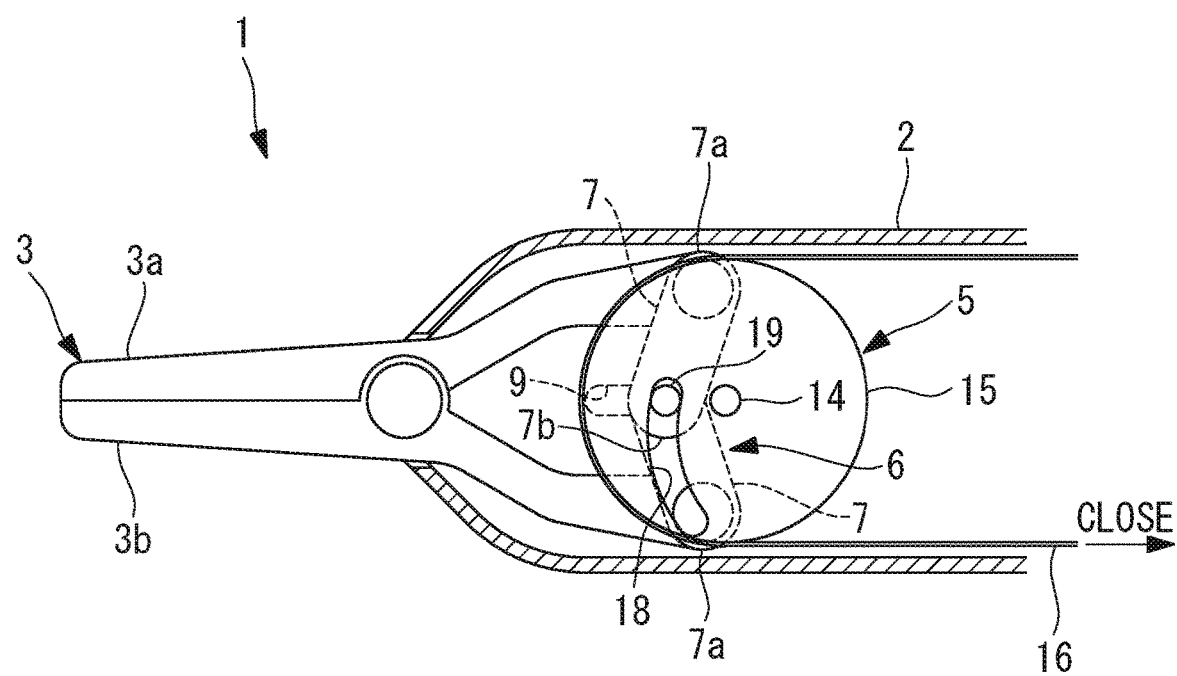
FIG. 9 is a longitudinal sectional view of the distal end portion of the medical treatment tool illustrated in FIG. 8, illustrating the operation of closing the distal ends of the grasping pieces.

Alternatively, as illustrated in FIGS. 8 and 9, the amplifying mechanism 5 may be configured by forming a cam groove 18 in the fixed pulley 15 and placing a shaft 19, which is fixed to the connecting shaft 8, inside the cam groove 18 instead of using the connecting link 17 illustrated in FIGS. 6 and 7. As illustrated in FIG. 8, the cam groove 18 is curved toward one direction in the circumferential direction of the fixed pulley 15 so as to gradually approach the radially inner side of the fixed pulley 15. The cam groove 18 guides the shaft 19 placed therein toward the distal end side or proximal end side along the slit 9 according to the rotation direction of the fixed pulley 15.

In this manner, as illustrated in FIG. 9, when a pulling force is applied to the wire 16 to rotate the fixed pulley 15, the shaft 19 moves toward the radially inner side along the cam groove 18. As a result, the distance (moment arm) between the direction in which the force is applied to the shaft 19 and the rotation center of the fixed pulley 15 decreases in a direction orthogonal to a line tangent to the cam groove 18, and thus the force applied to the shaft 19 can be amplified and input to the toggle mechanism 6.

As illustrated in FIG. 8, by pulling the segment of the wire 16 on the opposite side from that illustrated in FIG. 9, the shaft 19 can be pushed toward the distal end side, and the distal ends of the pair of grasping pieces 3a and 3b can be opened.

Figure 10:
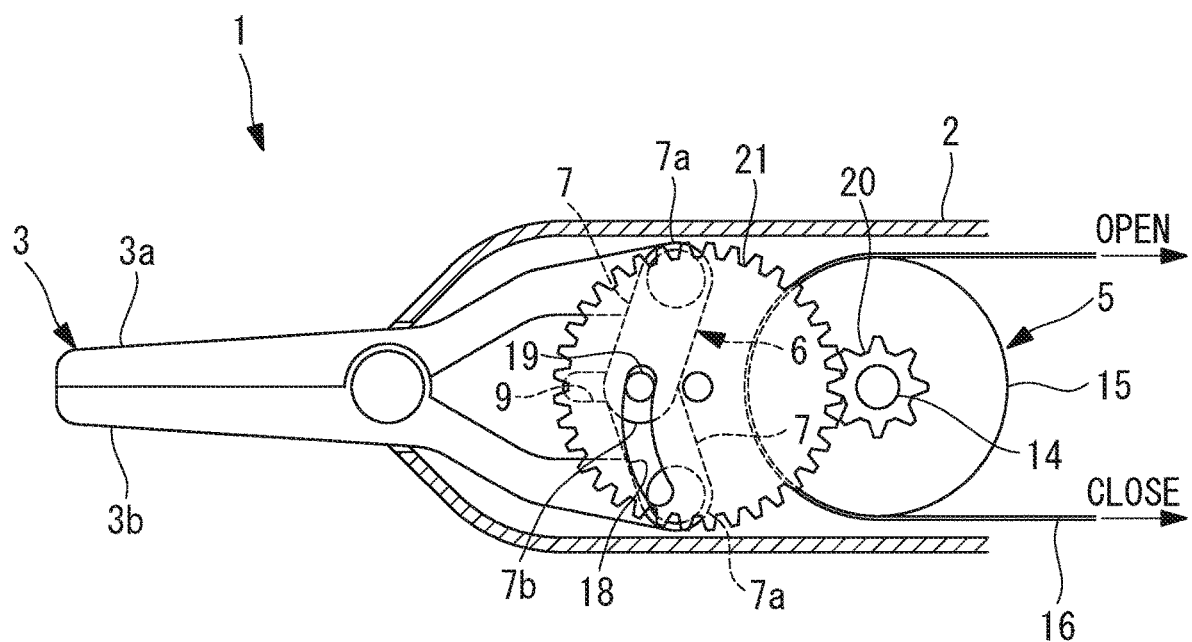
FIG. 10 is a longitudinal sectional view of a distal end portion illustrating a fourth modification of the medical treatment tool illustrated in FIG. 2.

As illustrated in FIG. 10, the amplifying mechanism 5 may be constituted by installing a drive gear 20 concentric with the fixed pulley 15 and forming the cam groove 18 in a driven gear 21 that meshes with the drive gear 20 instead of by forming the cam groove 18 in the fixed pulley 15. In this case, the relationship between the cam groove 18 in the driven gear 21 and the shaft 19 is the same as the relationship between the cam groove 18 in the fixed pulley 15 and the shaft 19 illustrated in FIGS. 8 and 9.

In the case illustrated in FIG. 10, the drive gear 20 has a small diameter, and the driven gear 21 has a large diameter. This provides an advantage in that the force of the drive gear 20 is transmitted to the driven gear 21 at a reduced speed, and thus the pulling force can be amplified by an amount corresponding to the reduction ratio. Another advantage is that when the diameter of the drive gear 20 is sufficiently small with respect to the fixed pulley 15, the diameter of the driven gear 21 can be increased to the diameter of the fixed pulley 15, and thus, an increase in the outer diameter of the insertion section 2 can be suppressed while obtaining a large reduction ratio.

Figure 11:
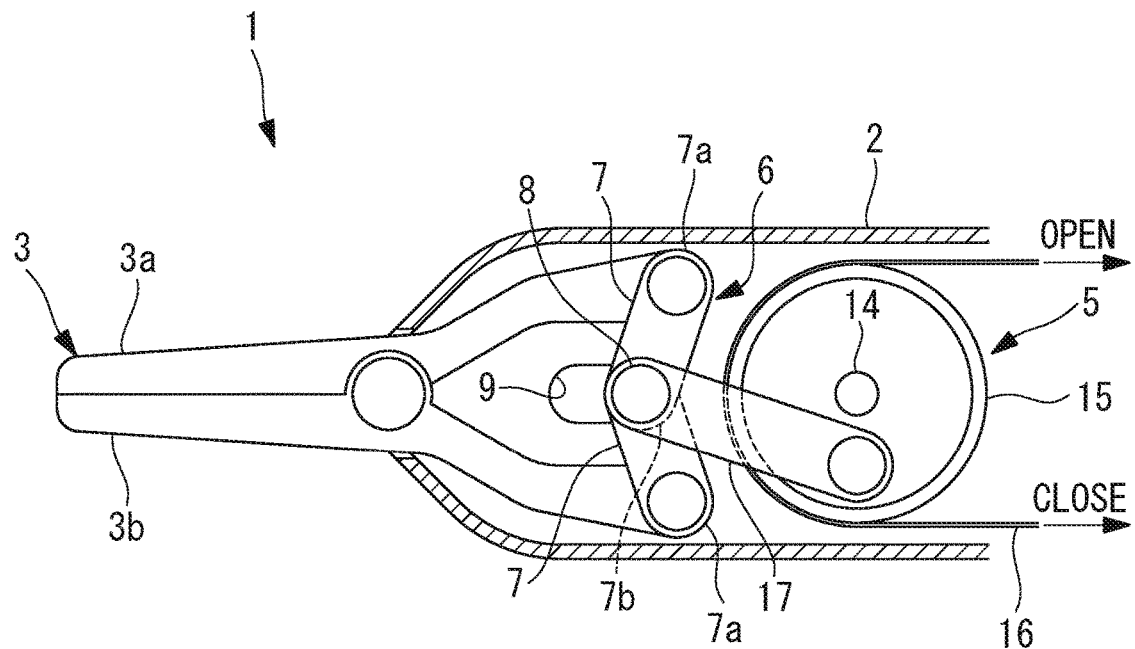
FIG. 11 is a longitudinal sectional view of a distal end portion illustrating a fifth modification of the medical treatment tool illustrated in FIG. 2.

Instead of the reducer constituted by the drive gear 20 and the driven gear 21, a planetary reducer that has one or more planetary gears (not illustrated) that mesh with a drive gear (input gear, not illustrated) concentric with the fixed pulley 15 may be employed, as illustrated in FIG. 11. In this case, the output shaft of the planetary reducer may be connected to the connecting shaft 8 of the link members 7 via the connecting link 17. Since the moment generated by the fixed pulley 15 by the pulling force applied to the wire 16 is amplified by the planetary reducer and input to the toggle mechanism 6, the grasping force of the grasping unit 3 can be improved, and the diameter of the insertion section 2 can be decreased.

Figure 12:
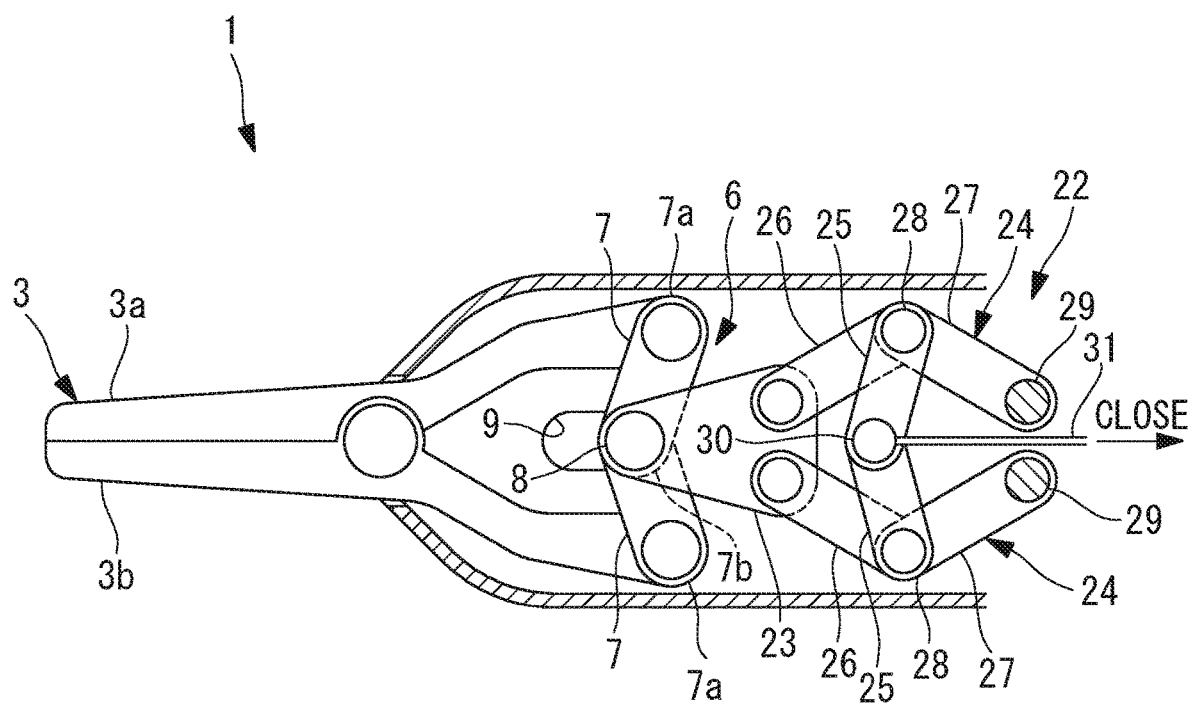
FIG. 12 is a longitudinal sectional view of a distal end portion illustrating a sixth modification of the medical treatment tool illustrated in FIG. 2.

Furthermore, as illustrated in FIG. 12, a second toggle mechanism 22 may be installed as the force amplifying mechanism 5 that amplifies the force input to the toggle mechanism 6. The second toggle mechanism 22 includes a connecting link 23 pivotably connected to the connecting shaft 8 of the link members 7 of the toggle mechanism 6, two sets of link units 24 arranged side-by-side in the radial direction on the proximal end side of the connecting link 23, and two link members 25 arranged to bridge between the link units 24.

Each of the two sets of link units 24 includes two link members 26 and 27, which are pivotably connected to each other at one ends with a connecting shaft 28. The other end of the link member 26 is pivotably connected to the connecting link 23, and the other end of the link member 27 is pivotably connected to a fixed shaft 29 fixed to the insertion section 2. One end of each of the two link members 25 is pivotably connected to connecting shaft 30 while the other end is pivotably connected to the connecting shaft 28 of the link unit 24.

The distal end of a wire-shaped force transmitting member 31 that can be pushed and pulled in the longitudinal direction from the proximal end side of the insertion section 2 is connected to the connecting shaft 30 of the two link members 25.

In this manner, the toggle mechanism 6 formed at the proximal ends of the grasping pieces 3a and 3b and the second toggle mechanism 22 connected in series to the toggle mechanism 6 both amplify the pulling force applied to the force transmitting member 31. Thus, there is an advantage in that while the increase in the lengths of the link members 7 and 25 of the toggle mechanisms 6 and 22 is suppressed to decrease the diameter, the grasping force of the grasping unit 3 can be improved.

The above-described embodiment also leads to the following invention.

According to an aspect of the present invention, there is provided a medical treatment tool including an elongated insertion section; a grasping unit supported by a distal end of the insertion section so as to be openable and closable; a driving unit disposed at a proximal end of the insertion section and generating a force to drive the grasping unit; a force transmitting member that transmits the force generated by the driving unit to the distal end of the insertion section; a force amplifying mechanism that amplifies the force transmitted through the force transmitting member; and a toggle mechanism that amplifies and converts the force amplified by the force amplifying mechanism into a force directed to open or close the grasping unit.

According to this aspect, the grasping unit at the distal end of the insertion section can be actuated and a treatment can be performed by inserting the flexible insertion section into the body and actuating the driving unit disposed at the proximal end of the insertion section. The force generated by the driving unit is transmitted to the distal end of the insertion section through the force transmitting member, amplified by the force amplifying mechanism, and then amplified and converted by the toggle mechanism into a force directed to open or close the grasping unit. As a result, the grasping unit opens and closes. The force input to the toggle mechanism is amplified by the force amplifying mechanism. Thus, the amplification ratio in the toggle mechanism can be decreased, the size of the toggle mechanism can be reduced, and the diameter of the insertion section can be decreased.

In the aspect described above, the force amplifying mechanism may amplify the force by reducing a speed at which the force transmitting member is moved by the force supplied by the force transmitting member.

In this manner, when the force generated by the driving unit is transmitted through the force transmitting member, the speed is reduced by the force amplifying mechanism and the force is thereby amplified and input to the toggle mechanism. Thus, the force can be amplified by merely decreasing the speed of the force supplied through transmission, and the structure can be simplified.

In the aspect described above, the grasping unit may include a pair of grasping pieces, at least one of which is rotatably supported relative to the insertion section. Moreover, the toggle mechanism may include a pair of link members each having a first end and a second end, the first ends being rotatably connected to proximal end portions of the respective grasping pieces, the second ends being rotatably connected to each other and being supported so as to be movable along a movement axis extending in a longitudinal direction of the insertion section. The link members may each have a length larger than a distance between the second end and the movement axis. A length of a line segment connecting the second end to a rotation center of the grasping pieces and being projected onto the movement axis may be smaller than a length of a line segment connecting the first end and the rotation center and being projected onto the movement axis.

In this manner, when the second ends of the toggle mechanism are moved toward the proximal end side along the longitudinal direction of the insertion section, the two link members respectively pivot on the first ends as the center, and the distance between the proximal end portions of the pair of grasping pieces having the first ends connected to each other is increased. Thus, at least one of the grasping pieces pivot about the rotation center, and the distal ends of the grasping pieces are closed. As the angle formed between the two link members approaches 180°, the force that acts to increase the distance between the proximal end portions of the pair of grasping pieces increases rapidly, and thus a large edge force can be generated at the distal ends of the grasping pieces.

In the aspect described above, the force transmitting member may be a wire that transmits a pulling force along the longitudinal direction of the insertion section, the force amplifying mechanism may include a movable pulley supported by the wire wrapping around the movable pulley so as to be movable in the longitudinal direction of the insertion section, the movable pulley having a rotation shaft connected to the second ends, and the wire may have a proximal end connected to the driving unit, may have two segments that extend substantially parallel to each other on respective sides of the movable pulley so as to flank the rotation shaft of the movable pulley, and may have another end fixed to the insertion section.

In this manner, when a pulling force is applied to the wire, a tension equal to the pulling force acts on each of the two segments of the wire extending substantially parallel to each other on respective sides of the movable pulley so as to flank the rotation shaft of the movable pulley, and thus, the rotation shaft of the movable pulley is pulled by a force twice the pulling force applied to the wire. In this manner, the force amplified to twice the pulling force can act on the second ends of the toggle mechanism to which the rotation shaft is connected. Thus, the lengths of the link members of the toggle mechanism can be suppressed, the diameter of the insertion section can be decreased, and large grasping force can be achieved.

In the aspect described above, the second ends of the pair of link members may be rotatably connected to each other at the rotation shaft of the movable pulley.

In this manner, a force twice the pulling force applied to the rotation shaft of the movable pulley can be directly input to the toggle mechanism.

In the aspect described above, the medical treatment tool may further include a fixed pulley attached so as to be rotatable about a shaft fixed to the insertion section, and the wire may be wound between the movable pulley and the fixed pulley.

In this manner, the multiplying factor of the force acting on the rotation shaft of the movable pulley can be set according to the number of turns of the wire wound between the movable pulley and the fixed pulley, and thus a larger force can be input to the toggle mechanism.

In the aspect described above, the force transmitting member may be a wire that transmits a pulling force along the longitudinal direction of the insertion section, and the force amplifying mechanism may include: a fixed pulley around which the wire is wrapped, the fixed pulley being supported so as to be rotatable about a shaft fixed to the insertion portion; and a connecting link having one end pivotably connected to a position in the fixed pulley such that a radius from this position is smaller than an outer radius of the fixed pulley, and another end pivotably connected to the second ends.

In this manner, when a pulling force is applied to the proximal end of the wire, a moment having a magnitude equal to the magnitude of the pulling force multiplied by the outer radius of the fixed pulley is generated in the fixed pulley. Meanwhile, a force having a magnitude equal to the aforementioned moment divided by the radius at the position of the second ends acts on the second ends of the connecting link connected to the fixed pulley. By setting the radius at the position of the second ends to be smaller than the outer radius of the fixed pulley, a force larger than the pulling force can act on the second ends of the connecting link, and the amplified pulling force can be input to the toggle mechanism.

In the aspect described above, the force transmitting member may be a wire that transmits a pulling force along the longitudinal direction of the insertion section, and the force amplifying mechanism may include: a fixed pulley around which the wire is wrapped, the fixed pulley being supported so as to be rotatable about a shaft fixed to the insertion section; and a cam groove that guides the second ends, the cam groove being formed in the fixed pulley and extending gradually radially inward along one direction in a circumferential direction.

In this manner, when a pulling force is applied to the proximal end of the wire, a moment having a magnitude equal to the magnitude of the pulling force multiplied by the outer radius of the fixed pulley is generated in the fixed pulley, and the fixed pulley turns. As the fixed pulley turns, the cam groove in the fixed pulley moves, and the second ends of the link members are guided by the cam groove and move in a direction approaching the rotation shaft of the fixed pulley. Thus, the moment arm is shortened, and the force acting on the second ends increases to balance the moments generated by the wire. As a result, the amplified pulling force can be input to the toggle mechanism.

In the aspect described above, the force transmitting member may be a wire that transmits a pulling force along the longitudinal direction of the insertion section, and the force amplifying mechanism may include: a fixed pulley around which the wire is wrapped, the fixed pulley being supported so as to be rotatable about a shaft fixed to the insertion section; a drive gear having a diameter smaller than an outer diameter of the fixed pulley and being fixed concentrically to the fixed pulley; a driven gear having a diameter larger than the diameter of the drive gear and being supported so as to be rotatable about the shaft fixed to the insertion section and mesh with the drive gear; and a cam groove that guides the second ends, the cam groove being formed in the driven gear and extending gradually radially inward along one direction in a circumferential direction.

In this manner, when a pulling force is applied to the proximal end of the wire, a moment having a magnitude equal to the magnitude of the pulling force multiplied by the outer radius of the fixed pulley is generated in the fixed pulley, and the fixed pulley turns. As a result, the drive gear concentrically fixed to the fixed pulley turns, and the driven gear meshed with the drive gear also turns. Since the diameter of the driven gear is larger than that of the drive gear, the moment is amplified as the two gears mesh. As the driven gear turns, the cam groove in the driven gear moves, and the second ends of the link members are guided by the cam groove and move in a direction approaching the shaft of the driven gear. Thus, the moment arm is shortened, and the force acting on the second ends increases to balance the moments generated by the wire. As a result, the double-amplified pulling force can be input to the toggle mechanism.

In the aspect described above, the force transmitting member may be a wire that transmits a pulling force along the longitudinal direction of the insertion section, and the force amplifying mechanism may include: a fixed pulley around which the wire is wrapped, the fixed pulley being supported so as to be rotatable about a shaft fixed to the insertion section; a planetary reducer equipped with an input gear concentrically fixed to the fixed pulley and a planetary gear that meshes with the input gear; and a connecting link having one end pivotably connected to a position remote from a center of an output shaft of the planetary reducer and another end pivotably connected to the second ends.

In this manner, when a pulling force is applied to the proximal end of the wire, a moment having a magnitude equal to the magnitude of the pulling force multiplied by the outer radius of the fixed pulley is generated in the fixed pulley, and the fixed pulley turns. As a result, the input gear concentrically fixed to the fixed pulley turns, and output is made as the speed of rotation of the input gear is reduced by the planetary reducer equipped with the planetary gear that meshes with the input gear. As a result, a force obtained by amplifying the pulling force applied to the wire can act on one end of the connecting link connected to the output shaft, and the amplified force can be input to the toggle mechanism connected to the other end of the connecting link.

In the aspect described above, the force amplifying mechanism may be a second toggle mechanism disposed between the force transmitting member and the toggle mechanism.

In this manner, since the force is double-amplified by the toggle mechanisms installed in series, the toggle mechanisms can be made smaller, the diameter can be decreased, and a large grasping force can be achieved.

REFERENCE SIGNS LIST 1 medical treatment tool
2 insertion section
3 grasping unit
3a, 3b grasping piece
4, 16 wire
5 amplifying mechanism (force amplifying mechanism)
6 toggle mechanism
7 link member
8 connecting shaft (rotation shaft)
7a end (first end)
7b end (second end)
10 movable pulley
14 shaft
15 fixed pulley
17 connecting link
18 cam groove
20 drive gear 21 driven gear
22 second toggle mechanism (force amplifying mechanism)
31 force transmitting member
40 driving unit

The invention claimed is:

1. A medical treatment tool comprising:
an elongated insertion section;
a grasper supported by a distal end of the insertion section so as to be openable and closable, the grasper including a pair of grasping pieces, at least one of which is rotatably supported relative to the insertion section;
a generator disposed at a proximal end of the insertion section and generating a force to drive the grasper;
a transmitter transmitting the force generated by the generator to the distal end of the insertion section;
an amplifier amplifying the force transmitted through the transmitter; and
a toggle amplifying and converting the force amplified by the amplifier into a force directed to open or close the grasper,
wherein the toggle includes a pair of links each having a first end and a second end, the first ends being rotatably connected to proximal end portions of the respective grasping pieces, the second ends being rotatably connected to each other and being supported so as to be movable along a movement axis extending in a longitudinal direction of the insertion section; the pair of links have a length larger than a distance between the first end and the movement axis; and each second end is disposed further distally than a corresponding first end in the longitudinal direction of the insertion section,
the transmitter is a wire that transmits a pulling force along the longitudinal direction of the insertion section,
the amplifier includes a movable pulley supported by the wire wrapping around the movable pulley so that the movable pulley is movable in the longitudinal direction of the insertion section, the movable pulley having a rotation shaft directly connected to the second ends of the pair of links and
the wire has a proximal end connected to the generator, has two segments that extend substantially parallel to each other on respective sides of the movable pulley so as to flank the rotation shaft of the movable pulley, and has another end fixed to the insertion section.

2. The medical treatment tool according to claim 1, wherein the amplifier amplifies the force by reducing a speed at which the transmitter is moved.

3. The medical treatment tool according to claim 1, wherein the second ends of the pair of links are rotatably connected to each other at the rotation shaft of the movable pulley.

4. The medical treatment tool according to claim 1, further comprising a fixed pulley attached so as to be rotatable about a shaft fixed to the insertion section,
wherein the wire is wound between the movable pulley and the fixed pulley.

* * * * *